(12) United States Patent
Cupka

(10) Patent No.: US 8,093,472 B2
(45) Date of Patent: Jan. 10, 2012

(54) INBRED CORN LINE MM27

(75) Inventor: Timothy Brian Cupka, Lebanon, IN (US)

(73) Assignees: Limagrain Europe S.A., Verneuil l'Etang (FR); KWS Saat AG, Einbeck (DE)

( * ) Notice: Subject to any disclaimer, the term of this patent is extended or adjusted under 35 U.S.C. 154(b) by 794 days.

(21) Appl. No.: 12/046,611

(22) Filed: Mar. 12, 2008

(65) Prior Publication Data

US 2009/0235383 A1    Sep. 17, 2009

(51) Int. Cl.
*A01H 5/00* (2006.01)
*A01H 5/10* (2006.01)
*A01H 1/02* (2006.01)
*C12N 15/82* (2006.01)

(52) U.S. Cl. .............. 800/320.1; 800/267; 800/275; 800/279; 800/284; 800/289; 800/300.1; 800/302; 435/412; 435/424; 435/430.1

(58) Field of Classification Search .................. None
See application file for complete search history.

(56) References Cited

U.S. PATENT DOCUMENTS

| | | | |
|---|---|---|---|
| 5,304,719 A | 4/1994 | Segebart |
| 5,367,109 A | 11/1994 | Segebart |
| 5,523,520 A | 6/1996 | Hunsperger et al. |
| 5,932,787 A | 8/1999 | Schuetz et al. |
| 6,025,547 A | 2/2000 | Stucker |
| 6,096,953 A | 8/2000 | Hoffbeck |
| 6,281,414 B1 | 8/2001 | Foley |
| 6,444,882 B1 | 9/2002 | Bowen |
| 6,452,074 B1 | 9/2002 | Ruaud |
| 6,747,194 B2 | 6/2004 | Koehring |
| 6,747,195 B2 | 6/2004 | Frederickson et al. |
| 6,753,465 B2 | 6/2004 | Bourrier |
| 6,765,133 B2 | 7/2004 | Koehring |
| 6,797,869 B2 | 9/2004 | Russel et al. |
| 7,084,333 B1 | 8/2006 | Brokish |
| 7,084,334 B1 | 8/2006 | Brokish |
| 7,166,785 B2 | 1/2007 | Gatti |
| 7,479,587 B2 | 1/2009 | Brokish |
| 7,482,517 B2 | 1/2009 | Bowen et al. |
| 7,491,874 B2 | 2/2009 | Brokish |
| 7,511,199 B2 | 3/2009 | Cupka |
| 7,605,310 B2 | 10/2009 | Brokish |
| 7,687,688 B2 | 3/2010 | Schuetz |
| 7,696,417 B2 | 4/2010 | Van der Reijden |

OTHER PUBLICATIONS

U.S. Appl. No. 11/672,079, filed Aug. 7, 2008, Brokish, H.
U.S. Appl. No. 12/046,611, filed Sep. 17, 2009, Cupka, T. et al.
U.S. Appl. No. 12/402,029, filed Sep. 16, 2010, Koehring, W.
U.S. Appl. No. 12/463,220, filed Nov. 11, 2010, Brokish, H.
U.S. Appl. No. 12/467,905, filed Nov. 18, 2010, Cupka, T.
U.S. Appl. No. 12/507,554, filed Jan. 27, 2011, Koehring, W.
U.S. Appl. No. 12/507,658, filed Jan. 27, 2011, Koehring, W.
U.S. Appl. No. 12/507,675, filed Jan. 27, 2011, Van den Reijen, A.
U.S. Appl. No. 12/535,152, filed Feb. 10, 2011, Whitehead, F.
U.S. Appl. No. 12/535,119, filed Feb. 10, 2011, Whitehead, F.
Allard, 1960. Principles of Plant Breeding. John Wiley & Sons, Inc. p. 55.
Darnell, et al., 1990. DNA Replication, Repair and Recombination. In Molecular Cell Biology, $2^{nd}$ Edition, W. H. Freeman and Company, p. 478.
Eshed, et al., 1996. Less-than-additive epistatic interactions of quantitative trait loci in tomato. Genetics. 143:1807-1817.
Kraft, et al., 2000. Linkage disequilibrium and fingerprinting in sugar beet. Theor. Appl. Genet. 101:323-326.
Murray, et al., 1988. Restriction fragment length polymorphisms: What are they and how can breeders use them? Proceedings of the $43^{rd}$ Annual Corn and Sorghum Industry Research Conference. 43:72-87.
Napoli, et al., 1990. Introduction of a chimeric chalcone synthase gene into petunia results in reversible co-suppression of homologous genes in trans. The Plant Cell. 2:279-289.
Phillips, et al., In Corn and Corn Improvement, ASA Monograph No. 18, $3^{rd}$ edition, p. 358, (1988).

*Primary Examiner* — David T Fox
(74) *Attorney, Agent, or Firm* — Jondle & Associates, P.C.

(57) ABSTRACT

An inbred corn line, designated MM27, is disclosed. The invention relates to the seeds of inbred corn line MM27, to the plants and plant parts of inbred corn line MM27 and to methods for producing a corn plant, either inbred or hybrid, by crossing the inbred line MM27 with itself or another corn line. The invention further relates to methods for producing a corn plant containing in its genetic material one or more transgenes and to the transgenic plants produced by that method and to methods for producing other inbred corn lines derived from the inbred MM27.

28 Claims, No Drawings

INBRED CORN LINE MM27

BACKGROUND OF THE INVENTION

The present invention relates to a new and distinctive corn inbred line, designated MM27. All publications cited in this application are herein incorporated by reference.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, resistance to diseases and insects, better stalks and roots, tolerance to drought and heat, reduction of grain moisture at harvest as well as better agronomic quality. With mechanical harvesting of many crops, uniformity of plant characteristics such as germination and stand establishment, growth rate, maturity and plant and ear height is important.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection, and backcross breeding.

The complexity of inheritance influences choice of breeding method. Backcross breeding is used to transfer one or a few favorable genes for a heritable trait into a desirable cultivar. This approach has been used extensively for breeding disease-resistant cultivars; nevertheless, it is also suitable for the adjustment and selection of morphological characters, color characteristics and simply inherited quantitative characters such as earliness, plant height or seed size and shape. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested per se and in hybrid combination and compared to appropriate standards in environments representative of the commercial target area(s) for three or more years. The best lines are candidates for use as parents in new commercial cultivars; those still deficient in a few traits may be used as parents to produce new populations for further selection.

These processes, which lead to the final step of marketing and distribution, usually take from eight to twelve years from the time the first cross is made. Therefore, development of new cultivars is a time-consuming process that requires precise forward planning, efficient use of resources, and a focus on clear objectives.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of corn breeding is to develop new, unique and superior corn inbred lines and hybrids. The breeder initially selects and crosses two or more parental lines, followed by repeated self pollination or selfing and selection, producing many new genetic combinations. The breeder can theoretically generate billions of different genetic combinations via crossing, selfing and mutations.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. This unpredictability results in the expenditure of large research funds to develop a superior new corn inbred line.

The development of commercial corn hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$s or by intercrossing two $F_1$s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, *Principles of Plant Breeding*, John Wiley and Son, pp. 115-161, 1960, Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the $F_1$ progeny. A double-cross hybrid is produced from four inbred lines crossed in pairs (A×B and C×D) and then the two $F_1$ hybrids are crossed again (A×B)×(C×D). Much of the hybrid vigor exhibited by $F_1$ hybrids is lost in the next generation ($F_2$). Consequently, seed from hybrid varieties is not used for planting stock.

Hybrid corn seed is typically produced by a male sterility system or by incorporating manual or mechanical detasseling. Alternate strips of two corn inbreds are planted in a field, and the pollen-bearing tassels are removed from one of the inbreds (female). Providing that there is sufficient isolation from sources of foreign corn pollen, the ears of the detasseled inbred will be fertilized only from the other inbred (male), and the resulting seed is therefore hybrid and will form hybrid plants.

The laborious, and occasionally unreliable, detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in corn plants, since only the female provides cytoplasm to the fertilized seed. CMS plants are fertilized with pollen from another inbred that is not male-sterile. Pollen from the second inbred may or may not contribute genes that make the hybrid plants male-fertile. Seed from detasseled fertile corn and CMS produced seed of the same hybrid can be blended to insure that adequate pollen loads are available for fertilization when the hybrid plants are grown.

There are several methods of conferring genetic male sterility available, such as multiple mutant genes at separate locations within the genome that confer male sterility, as disclosed in U.S. Pat. Nos. 4,654,465 and 4,727,219 to Brar et al. These and all patents referred to are incorporated by reference. In addition to these methods, Albertsen et al., U.S. Pat. No. 5,432,068, have developed a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

There are many other methods of conferring genetic male sterility in the art, each with its own benefits and drawbacks. These methods use a variety of approaches such as delivering into the plant a gene encoding a cytotoxic substance associated with a male tissue specific promoter or an anti-sense system in which a gene critical to fertility is identified and an antisense to that gene is inserted in the plant (see, Fabinjanski, et al. EPO 89/0301053.8 publication no. 329,308 and PCT application PCT/CA90/00037 published as WO 90/08828).

Another version useful in controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, G. R., U.S. Pat. No. 4,936,904). Application of the gametocide, timing of the application, and genotype often limit the usefulness of the approach.

Corn is an important and valuable field crop. Thus, a continuing goal of plant breeders is to develop stable, high yielding corn hybrids that are agronomically sound. The reasons for this goal are obviously to maximize the amount of ears or kernels produced on the land used and to supply food for both humans and animals. To accomplish this goal, the corn breeder must select and develop corn plants that have the traits that result in superior parental lines for producing hybrids.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary and illustrative, not limiting in scope. In various embodiments, one or more of the above-described problems have been reduced or eliminated, while other embodiments are directed to other improvements.

According to the invention, there is provided an inbred corn line, designated MM27. This invention thus relates to the seeds of inbred corn line MM27, to the plants or parts thereof of inbred corn line MM27, to plants or parts thereof having all the physiological and morphological characteristics of inbred corn line MM27 and to plants or parts thereof having all the physiological and morphological characteristics of inbred corn line MM27 listed in Table 1. Parts of the inbred corn plant of the present invention are also provided, such as e.g., pollen obtained from an inbred plant and an ovule of the inbred plant.

In another aspect, the present invention provides regenerable cells for use in tissue culture of inbred corn plant MM27. The tissue culture will preferably be capable of regenerating plants having all the physiological and morphological characteristics of the foregoing inbred corn plant. Preferably, the cells of such tissue cultures will be embryos, meristematic cells, seeds, callus, pollen, leaves, anthers, roots, root tips, silk, flowers, kernels, ears, cobs, husks, stalks or the like. Protoplasts produced from such tissue culture are also included in the present invention. The corn plants regenerated from the tissue cultures are also part of the invention.

Also included in this invention are methods for producing a corn plant produced by crossing the inbred line MM27 with itself or another corn line. When crossed with itself, i.e. crossed with another inbred line MM27 plant or self pollinated, the inbred line MM27 will be conserved. When crossed with another, different corn line, an $F_1$ hybrid seed is produced. $F_1$ hybrid seeds and plants produced by growing said hybrid seeds are included in the present invention. A method for producing a $F_1$ hybrid corn seed comprising crossing inbred line MM27 corn plant with a different corn plant and harvesting the resultant hybrid corn seed are also part of the invention. The hybrid corn seed produced by the method comprising crossing inbred line MM27 corn plant with a different corn plant and harvesting the resultant hybrid corn seed are included in the invention, as are included the hybrid corn plant or parts thereof, seeds included, produced by growing said hybrid corn seed.

In another embodiment, this invention relates to a method for producing the inbred line MM27 from a collection of seeds, the collection containing both inbred line MM27 seeds and hybrid seeds having MM27 as a parental line. Such a collection of seed might be a commercial bag of seeds. Said method comprises planting the collection of seeds. When planted, the collection of seeds will produce inbred line MM27 plants from inbred line MM27 seeds and hybrid plant from hybrid seeds. The plants having all the physiological and morphological characteristics of corn inbred line MM27 or having a decreased vigor compared to the other plants grown from the collection of seeds are identified as inbred line MM27 parent plants. Said decreased vigor is due to the inbreeding depression effect and can be identified for example by a less vigorous appearance for vegetative and/or reproductive characteristics including shorter plant height, small ear size, ear and kernel shape, ear color or other characteristics. As previously mentioned, if the inbred line MM27 is self-pollinated, the inbred line MM27 will be preserved, therefore, the next step is controlling pollination of the inbred parent plants in a manner which preserves the homozygosity of said inbred line MM27 parent plant, and the final step is to harvest the resultant seed.

This invention also relates to methods for producing other inbred corn lines derived from inbred corn line MM27 and to the inbred corn lines derived by the use of those methods.

In another aspect, the present invention provides transformed MM27 inbred corn line or parts thereof that have been transformed so that its genetic material contains one or more transgenes, preferably operably linked to one or more regulatory elements. Also, the invention provides methods for producing a corn plant containing in its genetic material one or more transgenes, preferably operably linked to one or more regulatory elements, by crossing transformed MM27 inbred corn line with either a second plant of another corn line, or a non-transformed corn plant of the inbred line MM27, so that the genetic material of the progeny that results from the cross contains the transgene(s), preferably operably linked to one or more regulatory elements. The invention also provides methods for producing a corn plant that contains in its genetic material one or more transgene(s), wherein the method comprises crossing the inbred corn line MM27 with a second plant of another corn line which contains one or more transgene(s) operably linked to one or more regulatory element(s) so that the genetic material of the progeny that results from the cross contains the transgene(s) operably linked to one or more regulatory element(s). Transgenic corn plants, or parts thereof produced by the method are in the scope of the present invention.

More specifically, the invention comprises methods for producing corn plants with at least one trait selected from the group consisting of male sterile corn plants, male fertile corn plants, herbicide resistant corn plants, insect resistant corn plants, disease resistant corn plants, water stress tolerant corn plants, or plants with modified, in particular decreased, phytate content, plants with modified waxy and/or amylose starch content, plants with modified protein content, plants with modified oil content or profile, plants with increased digestibility or plants with increased nutritional quality. Said methods comprise transforming the inbred line MM27 corn plant with nucleic acid molecules that confer male sterility, male fertility, herbicide resistance, insect resistance, disease resistance, water stress tolerance, or that can modify the phytate, the waxy and/or amylose starches, the protein or the oil contents, the digestibility or the nutritional qualities, respectively. The transformed corn plants obtained from the provided methods, including male sterile corn plants, male fertile corn plants, herbicide resistant corn plants, insect resistant corn plants, disease resistant corn plants, water stress tolerant corn plants, plants with modified phytate, waxy and/or amylose starches, protein or oil contents, plants with increased digestibility and plants with increased nutritional quality are included in the present invention. Plants may display one or more of the above listed traits. For the present invention and the skilled artisan, disease is understood to be fungal disease, viral disease, bacterial disease or other plant pathogenic diseases and disease resistant plant will encompass plants resistant to fungal, viral, bacterial and other plant pathogens.

Also included in the invention are methods for producing a corn plant containing in its genetic material one or more transgenes involved with fatty acid metabolism, carbohydrate metabolism, and starch content such as waxy starch or increased amylose starch. The transgenic corn plants produced by these methods are also part of the invention.

In another aspect, the present invention provides for methods of introducing one or more desired trait(s) into the corn line MM27 and plants obtained from such methods. The desired trait(s) may be, but not exclusively, a single gene, preferably a dominant but also a recessive allele. Preferably, the transferred gene or genes will confer such traits as male sterility, herbicide resistance, insect resistance, resistance for bacterial, fungal, or viral disease, male fertility, water stress tolerance, enhanced nutritional quality, modified waxy content, modified amylose content, modified protein content, modified oil content, enhanced plant quality, enhanced digestibility and industrial usage. The gene or genes may be naturally occurring maize gene(s) or transgene(s) introduced through genetic engineering techniques. The method for introducing the desired trait(s) is preferably a backcrossing process making use of a series of backcrosses to the inbred corn line MM27 during which the desired trait(s) is maintained by selection.

When using a transgene, the trait is generally not incorporated into each newly developed line such as MM27 by direct transformation. Rather, the more typical method used by breeders of ordinary skill in the art to incorporate the transgene is to take a line already carrying the transgene and to use such line as a donor line to transfer the transgene into the newly developed line. The same would apply for a naturally occurring trait. The backcross breeding process comprises the following steps: (a) crossing the inbred line MM27 plants with plants of another line that comprise the desired trait(s); (b) selecting the $F_1$ progeny plants that have the desired trait(s); (c) crossing the selected $F_1$ progeny plants with the inbred line MM27 plants to produce backcross progeny plants; (d) selecting for backcross progeny plants that have the desired trait(s) and physiological and morphological characteristics of corn inbred line MM27 to produce selected backcross progeny plants; and (e) repeating steps (c) and (d) one, two, three, four, five six, seven, eight, nine or more times in succession to produce selected, second, third, fourth, fifth, sixth, seventh, eighth, ninth or higher backcross progeny plants that comprise the desired trait(s) and all the physiological and morphological characteristics of corn inbred line MM27 as listed in Table 1. The corn plants produced by the methods are also part of the invention. Backcrossing breeding methods, well known to one skilled in the art of plant breeding will be further developed in subsequent parts of the specification.

In another aspect of the invention, corn inbred MM27 may be used as a parent, or a single gene conversion or a transgenic inbred line of MM27, such as MM27BT1, may be used as a parent and may be crossed with another corn line including but not limited to the following corn lines: BB14, CB1, BB38, BB45, BB47, BB53, BB57, BB59, BC5, HXN110RR2, HXN112CRWRR2, HXN11RR2, RBO1BT1, TR7245HX1-1 and BC109. Corn inbred MM27 may be used as a parent or a single gene conversion or a transgenic inbred line of MM27 such as MM27BT1 may be used as a parent and may be crossed with another corn line including but not limited to the following corn lines: single gene conversions or transgenic inbred lines of BB14, such as BB14MON88017, single gene conversions or transgenic inbred lines of BC5, such as BC5 MON88017, single gene conversions or transgenic inbred lines of CB1, such as CB1MON88017, and single gene conversions or transgenic inbred lines of BB38, such as BB38MON88017, and single gene conversions or transgenic inbred lines of BB45, such as BB45MON88017, and single gene conversions or transgenic inbred lines of BB47, such as BB47MON88017, and single gene conversions or transgenic inbred lines of BB53, such as BB53MON88017, and single gene conversions or transgenic inbred lines of BB57, such as BB57MON88017, and single gene conversions or transgenic inbred lines of BB59, such as BB59MON88017, and single gene conversions or transgenic inbred lines of BC5, such as BC5MON88017, and single gene conversions or transgenic inbred lines of HXN110RR2, such as HXN110MON88017, and single gene conversions or transgenic inbred lines of HXN112CRWRR2, such as HXN112MON88017, and single gene conversions or transgenic inbred lines of RBO1, such as RBO1MON88017, and single gene conversions or transgenic inbred lines of TR7245HX1, such as TR7245HXT, and single gene conversions or transgenic inbred lines of BC109, such as BC109MON88017. Preferably, the single gene conversions or transgenic inbred lines will confer such traits as male sterility, herbicide resistance, insect resistance, resistance for bacterial, fungal, or viral disease, male fertility, water stress tolerance, enhanced nutritional quality, modified waxy content, modified amylose content, modified protein content, modified oil content, enhanced plant quality, enhanced digestibility and industrial usage. The gene or genes may be naturally occurring maize gene(s) or transgene(s) introduced through genetic engineering techniques. The hybrid corn plants having corn inbred MM27 or a single gene conversion or a transgenic inbred line of MM27 as a parental line and having another, different, corn line as a second parental line as discussed above are comprised in the present invention.

Any DNA sequence(s), whether from a different species or from the same species that is inserted into the genome using transformation is referred to herein collectively as "transgenes". In some embodiments of the invention, a transformed variant of MM27 may contain at least one transgene but could contain at least 1, 2, 3, 4, 5, 6, 7, 8, 9, or 10 transgenes.

In an embodiment of this invention is a method of making a backcross conversion of corn inbred line MM27, comprising the steps of crossing a plant of corn inbred line MM27 with a donor plant comprising a mutant gene or transgene conferring a desired trait, selecting an F1 progeny plant comprising the mutant gene or transgene conferring the desired trait, and backcrossing the selected F1 progeny plant to a plant of corn inbred line MM27. This method may further comprise the step of obtaining a molecular marker profile of corn inbred line MM27 and using the molecular marker profile to select for a progeny plant with the desired trait and the molecular marker profile of MM27. In the same manner, this method may be used to produce an F1 hybrid seed by adding a final step of crossing the desired trait conversion of corn inbred line MM27 with a different corn plant to make F1 hybrid corn seed comprising a mutant gene or transgene conferring the desired trait.

In some embodiments of the invention, the number of loci that may be backcrossed into MM27 is at least 1, 2, 3, 4, or 5. A single loci may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci.

In a preferred embodiment, the present invention provides methods for increasing and producing inbred line MM27 seed, whether by crossing a first inbred parent corn plant with a second inbred parent corn plant and harvesting the resultant corn seed, wherein both said first and second inbred corn plant are the inbred line MM27 or by planting an inbred corn seed of the inbred corn line MM27, growing an inbred line MM27 plant from said seed, controlling a self pollination of the plant where the pollen produced by the grown inbred line MM27 plant pollinates the ovules produced by the very same inbred line MM27 grown plant and harvesting the resultant seed.

The invention further provides methods for developing corn plants in a corn plant breeding program using plant breeding techniques including recurrent selection, backcrossing, pedigree breeding, molecular marker (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs). Amplified Fragment Length Polymorphisms (AFLPs), and Simple Sequence Repeats (SSRs) which are also referred to as Microsatellites, etc.) enhanced selection, genetic marker enhanced selection and transformation. Corn seeds, plants, and parts thereof produced by such breeding methods are also part of the invention.

In addition to the exemplary aspects and embodiments described above, further aspects and embodiments will become apparent by study of the following descriptions.

Definitions

In the description and tables which follow, a number of terms are used. In order to provide a clear and consistent understanding of the specification and claims, including the scope to be given such terms, the following definitions are provided:

Allele. The allele is any of one or more alternative forms of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Collection of seeds. In the context of the present invention a collection of seeds will be a grouping of seeds mainly containing similar kind of seeds, for example hybrid seeds having the inbred line of the invention as a parental line, but that may also contain, mixed together with this first kind of seeds, a second, different kind of seeds, of one of the inbred parent lines, for example the inbred line of the present invention. A commercial bag of hybrid seeds having the inbred line of the invention as a parental line and containing also the inbred line seeds of the invention would be, for example such a collection of seeds.

Daily heat unit value. The daily heat unit value is calculated as follows: (the maximum daily temperature+the minimum daily temperature)/2 minus 50. All temperatures are in degrees Fahrenheit. The maximum temperature threshold is 86 degrees, if temperatures exceed this, 86 is used. The minimum temperature threshold is 50 degrees, if temperatures go below this, 50 is used.

Decreased vigor. A plant having a decreased vigor in the present invention is a plant that, compared to other plants has a less vigorous appearance for vegetative and/or reproductive characteristics including shorter plant height, small ear size, ear and kernel shape, ear color or other characteristics.

Dropped Ears. This is a measure of the number of dropped ears per plot, and represents the percentage of plants that dropped an ear prior to harvest.

Dry down. This is the rate at which a hybrid will reach acceptable harvest moisture Ear Height. The ear height is a measure from the ground to the upper ear node attachment, and is measured in centimeters.

Essentially all of the physiological and morphological characteristics. A plant having essentially all of the physiological and morphological characteristics means a plant having the physiological and morphological characteristics of the recurrent parent, except for the characteristics derived from the converted gene.

GDU pollen. The number of heat units from planting until 50% of the plants in the hybrid are shedding pollen.

GDU Silk. The GDU silk (=heat unit silk) is the number of growing degree units (GDU) or heat units required for an inbred line or hybrid to reach silk emergence from the time of planting. Growing degree units are calculated by the Barger Method, where the heat units for a 24-hour period are: GDU= ((Max Temp+Min Temp)/2)−50 The highest maximum used is 86° F. and the lowest minimum used is 50° F. For each hybrid, it takes a certain number of GDUs to reach various stages of plant development. GDUs are a way of measuring plant maturity. GDUs can also relate to stages of growth for an inbred line.

Harvest Aspect. This is a visual rating given the day of harvest or the previous day. Hybrids are 1 (poorest) to 9 (best) with poorer scores given for poor plant health, visible signs of fungal infection, poor plant intactness characterized by missing leaves, tassels, or other vegetative parts, or a combination of these traits.

Herbicide resistant or tolerant. A plant containing any herbicide-resistant gene or any DNA molecule or construct (or replicate thereof) which is not naturally occurring in the plant which results in increase tolerance to any herbicide including, imidazoline, sulfonylurea, glyphosate, glufosinate, L-phosphinothricin, triazine and benzonitrile. For purposes of this definition, a DNA molecule or construct shall be considered to be naturally occurring if it exists in a plant at a high enough frequency to provide herbicide resistance without further selection and/or if it has not been produced as a result of tissue culture selection, mutagenesis, genetic engineering using recombinant DNA techniques or other in vitro or in vivo modification to the plant.

HTU. HTU is the summation of the daily heat unit value calculated from planting to harvest.

Inbreeding depression. The inbreeding depression is the loss of performance of the inbreds due to the effect of inbreeding, i.e. due to the mating of relatives or to self-pollination. It increases the homozygous recessive alleles leading to plants which are weaker and smaller and having other less desirable traits.

Late plant greenness. Similar to a stay green rating. This is a visual assessment given at around the dent stage but typically a few weeks before harvest to characterize the degree of greenness left in the leaves. Plants are rated from 1 (poorest) to 9 (best) with poorer scores given for plants that have more non-green leaf tissue typically due to early senescence or from disease.

MN RM. This represents the Minnesota Relative Maturity Rating (MN RM) for the hybrid and is based on the harvest moisture of the grain relative to a standard set of checks of previously determined MN RM rating. Regression analysis is used to compute this rating.

Moisture. The moisture is the actual percentage moisture of the grain at harvest.

Plant Cell. Plant cell, as used herein includes plant cells whether isolated, in tissue culture, or incorporated in a plant or plant part.

Plant habit. This is a visual assessment assigned during the late vegetative to early reproductive stages to characterize the plants leaf habit. It ranges from decumbent with leaves growing horizontally from the stalk to a very upright leaf habit, with leaves growing near vertically from the stalk.

Plant Height. This is a measure of the height of the hybrid from the ground to the tip of the tassel, and is measured in centimeters.

Plant intactness. This is a visual assessment assigned to a hybrid or inbred at or close to harvest to indicate the degree that the plant has suffered disintegration through the growing season. Plants are rated from 1 (poorest) to 9 (best) with poorer scores given for plants that have more of their leaf blades missing.

Plant Part. As used herein, the term "plant part" includes leaves, stems, roots, seeds, grains, embryos, pollens, ovules, flowers, ears, cobs, husks, stalks, root tips, anthers, silk, tissue, cells and the like.

Pollen shed. This is a visual rating assigned at flowering to describe the abundance of pollen produced by the anthers. Inbreds are rated 1 (poorest) to 9 (best) with the best scores for inbreds with tassels that shed more pollen during anthesis.

Post-anthesis Root Lodging. This is a percentage plants that root lodge after anthesis: plants that lean from the vertical axis at an approximately 30° angle or greater.

Pre-anthesis Brittle Snapping. This is a percentage of "snapped" plants following severe winds prior to anthesis Pre-anthesis Root Lodging. This is a percentage plants that root lodge prior to anthesis: plants that lean from the vertical axis at an approximately 30° angle or greater.

Predicted RM. This trait for a hybrid, predicted relative maturity (RM), is based on the harvest moisture of the grain. The relative maturity rating is based on a known set of checks and utilizes conventional maturity such as the Comparative Relative Maturity Rating System or its similar, the Minnesota Relative Maturity Rating System.

Quantitative Trait Loci (QTL) Quantitative trait loci refer to genetic loci that control to some degree numerically representable traits that are usually continuously distributed.

Regeneration. Regeneration refers to the development of a plant from tissue culture.

Root Lodging. The root lodging is the percentage of plants that root lodge; i.e., those that lean from the vertical axis at an approximate 30° angle or greater would be counted as root lodged.

Seed quality. This is a visual rating assigned to the kernels of the inbred. Kernels are rated 1 (poorest) to 9 (best) with poorer scores given for kernels that are very soft and shriveled with splitting of the pericarp visible and better scores for fully formed kernels.

Seedling Vigor. This is the vegetative growth after emergence at the seedling stage, approximately five leaves.

Silking ability. This is a visual assessment given during flowering. Plants are rated on the amount and timing of silk production. Plants are rated from 1 (poorest) to 9 (best) with poorer scores given for plants that produce very little silks that are delayed past pollen shed.

Single gene converted. Single gene converted or conversion plants refers to plants which are developed by a plant breeding technique called backcrossing wherein essentially all the morphological and physiological characteristics of an inbred are recovered in addition to the single gene transferred into the inbred via the backcrossing technique or via genetic engineering. This also includes multiple transference of single genes.

Stalk Lodging. This is the percentage of plants that stalk lodge, i.e., stalk breakage, as measured by either natural lodging or pushing the stalks and determining the percentage of plants that break off below the ear. This is a relative rating of a hybrid to other hybrids for standability.

Standability. A term referring to the how well a plant remains upright towards the end of the growing season. Plants with excessive stalk breakage and/or root lodging would be considered to have poor standability.

Stay Green. Stay green is the measure of plant health near the time of black layer formation (physiological maturity). A high score indicates better late-season plant health.

Transgenic. Where an inbred line has been converted to contain one or more transgenes by single gene conversion or by direct transformation.

Variety. A plant variety as used by one skilled in the art of plant breeding means a plant grouping within a single botanical taxon of the lowest known rank which can be defined by the expression of the characteristics resulting from a given genotype or combination of phenotypes, distinguished from any other plant grouping by the expression of at least one of the said characteristics and considered as a unit with regard to its suitability for being propagated unchanged (International convention for the protection of new varieties of plants)

Yield (Bushels/Acre). The yield is the actual yield of the grain at harvest adjusted to 15.5% moisture.

DETAILED DESCRIPTION OF THE INVENTION

Inbred corn line MM27 is a yellow dent corn inbred with superior characteristics, and provides an excellent male parental line in crosses for producing first generation ($F_1$) hybrid corn. Inbred corn line MM27 is best adapted to the East, Central, Western and Southern regions of the United States Corn Belt commonly referred to as Zones 5 and 9. Hybrids that are adapted to these maturity zones can be grown on a very significant number of acres as it relates to the total of the USA corn acres. MM27 can be used to produce hybrids having a relative maturity of approximately 104 to 116 days on the Comparative Relative Maturity Rating System for harvest moisture of grain. MM27 produces an abundant volume of pollen as a male parent in the production of $F_1$ hybrids. MM27 contributes good health to the $F_1$ hybrids which results in excellent root strength in the $F_1$ hybrids along with an appealing look at harvest. This in turn allows farmers to harvest more efficiently and reduces field losses compared to hybrids that have inferior roots and poor plant health. MM27 also contributes an excellent yield to moisture ratio to the $F_1$ hybrids when compared to other MO17/Non Stiff Stalk based inbreds. The high yield to moisture ratio for its maturity and level of production directly correlate to a higher income per acre for the farmer as it relates to high yields with minimal drying costs. $F_1$ hybrids that have MM27 as one of the parent lines produce girthy ears with a high number of kernel rows and kernels that are very long/deep. MM27 contributes very good harvest appearance to the $F_1$ hybrids which relates directly to higher levels of plant intactness for the farmer at harvest. This plant intactness improves harvest efficiency. The high kernel row number along with the deep/long kernels are reflected in the high yields that the $F_1$ hybrids produce. Good agronomics and good intactness in the $F_1$ hybrids along with a very uniform and an appealing look at harvest are some of the observed qualities. The harvest appearance of a hybrid is a visual rating taking at the time of harvest. Rapid grain fill and fast drydown allows farmers to harvest more efficiently, lowers the costs of drying and reduces field losses compared to hybrids that must remain in the field longer to reach an acceptable harvest moisture. The rapid drydown of the $F_1$ hybrids directly correlates to the positive yield to moisture ratio. MM27 provides the $F_1$ hybrid with high levels of drought and stress tolerance as observed in the testing locations where these conditions were present.

MM27 is similar to MO17, however, there are numerous differences including the fact that MM27 is appreciably shorter on a line per se basis, has a lower ear insertion and contributes higher kernel row numbers and improved kernel depth/length. MM27 contributes to appreciably faster grain fill and drydown than other commonly used MO17 or C123 derived inbreds such as LH287.

MM27 has a plant height of 190 cm with an average ear insertion of 70 cm. The MM27 consistency of ear height and ear girth are transferred to the $F_1$ hybrids in the majority of crosses and are exhibited in an eye-appealing appearance, especially at harvest time. MM27 is a mid-season inbred. Heat units to 50% pollen shed are approximately 1359 and to 50% silk are approximately 1425 as measured near Lebanon, Ind. in 2006 and 2007.

MM27 is an inbred line with very high yield potential in hybrids. Hybrids with MM27 as one parental line produce very uniform, large ears with a high kernel row number and rapid drydown. These hybrid combinations result in excellent yield to moisture ratios and under most conditions minimize drying costs when compared to inbred lines of similar maturity and family background.

Some of the criteria used to select ears in various generations include: yield, yield to harvest moisture ratio, stalk quality, root quality, disease tolerance with emphasis on grey leaf spot, test weight, late season plant greenness, late season plant intactness, ear retention, ear height, pollen shedding ability, silking ability, and corn borer tolerance. The rate of grain fill and rapid drydown in hybrids with MM27 tend to consistently demonstrate above average ratings. During the development of the line, crosses were made to inbred testers for the purpose of estimating the line's general and specific combining ability, and evaluations were run by the Lebanon, Ind. Research Station. The inbred was evaluated further as a line and in numerous crosses by the Lebanon station and other research stations across the Corn Belt. The inbred has proven to have a good combining ability in hybrid combinations.

The inbred line has shown uniformity and stability for the traits, within the limits of environmental influence for the traits. MM27 was developed through the conventional recurrent selection breeding method. It has been self-pollinated a sufficient number of generations with careful attention to uniformity of plant type. The line has been increased with continued observation for uniformity. No variant traits have been observed or are expected in MM27.

Inbred corn line MM27 has the following morphologic and other characteristics (based primarily on data collected at Lebanon, Ind.).

TABLE 1

VARIETY DESCRIPTION INFORMATION

| | | |
|---|---|---|
| Type: | MM27 is a yellow, dent corn inbred | |
| Region where developed: | Lebanon, Indiana | |
| Maturity: | | |
| | Days | Heat Units |
| From emergence to 50% of plants in silk: | 55 | 1425 |
| From emergence to 50% of plants in pollen: | 53 | 1359 |
| Heat Units: = GDU = ((Max Temp + Min Temp)/2) − 50 | | |
| Plant: | | |
| Plant Height to tassel tip: | 190 cm | |
| Ear Height to base of top ear: | 70 cm | |
| Average Length of Top Ear Internode: | 15 cm | |
| Average number of Tillers: | 0 | |
| Average Number of Ears per Stalk: | 2.0 | |
| Anthocyanin of Brace Roots: | Present, moderate | |
| Leaf: | | |
| Width of Ear Node Leaf: | 10 cm | |
| Length of Ear Node Leaf: | 64 cm | |
| Number of leaves above top ear: | 6 | |
| Leaf Angle from 2nd Leaf above ear at anthesis to Stalk above leaf: | 45° | |
| Leaf Color: | Munsell 7.5GY-3/4 (soft-green) | |
| Leaf Sheath Pubescence (Rated on scale from 1 = none to 9 = like peach fuzz): | 4 | |
| Marginal Waves (Rated on scale from 1 = none to 9 = many): | 3 | |
| Longitudinal Creases (Rated on scale from 1 = none to 9 = many): | 5 | |
| Tassel: | | |
| Number of Lateral Branches: | 6 | |
| Branch Angle from Central Spike: | 45° | |
| Tassel Length (from top leaf collar to tassel top): | 33 cm | |

TABLE 1-continued

VARIETY DESCRIPTION INFORMATION

| | |
|---|---|
| Pollen Shed (Rated on scale from 0 = male sterile to 9 = heavy shed): | 9 |
| Anther Color: | Munsell 5Y-8/8 |
| Glume Color: | Munsell 2.5GY 7/4 |
| Tassel Glume Bands Color: | Absent |
| Ear: (Unhusked Data) | |
| Silk Color (3 days after emergence): | Munsell 10Y 9/8 |
| Fresh Husk Color (25 days after 50% silking): | Munsell 5GY 6/6 |
| Dry Husk Color (65 days after 50% silking): | Munsell 5Y 8/4 |
| Position of Ear: | Horizontal |
| Husk Tightness (Rated on scale from 1 = very loose to 9 = very tight): | 8 |
| Husk Extension at harvest: | Moderate husk extension, 2 cm |
| Ear: (Husked Ear Data) | |
| Ear Length: | 14.2 cm |
| Ear Diameter at mid-point: | 42.3 mm |
| Ear Weight: | 105.7 gm |
| Number of Kernel Rows: | 12-14 |
| Row Alignment: | Straight |
| Shank Length: | 2.0 cm |
| Ear Taper: | Cylindrical |
| Kernel: (Dried) | |
| Kernel Length: | 10.6 mm |
| Kernel Width: | 7.4 mm |
| Kernel Thickness: | 4.1 mm |
| Round Kernels (Shape Grade): | 29% |
| Aleurone Color: | White |
| Hard Endosperm Color: | Munsell 10YR 8/10 |
| Endosperm Type: | Dent |
| Weight per 100 kernels (unsized sample): | 28 gm |
| Cob: | |
| Cob Diameter at Mid-Point: | 24 mm |
| Cob Color: | Red |
| Agronomic Traits: | |
| Stay Green (at 65 days after anthesis) (Rated on scale from 1 = worst to 9 = excellent): | 6 |
| Dropped Ears (at 65 days after anthesis): | 0% |
| Pre-anthesis Brittle Snapping: | 0% |
| Pre-anthesis Root Lodging: | 0% |
| Post-anthesis Root Lodging (at 65 days after anthesis): | 0% |
| Yield of Inbred Per Se (at 12-13% grain moisture): | 65 Bu/Acre |

Further Embodiments of the Invention

This invention is also directed to methods for producing a corn plant by crossing a first parent corn plant with a second parent corn plant wherein either the first or second parent corn plant is an inbred corn plant of the line MM27. Further, both first and second parent corn plants can come from the inbred corn line MM27. When self-pollinated, or crossed with another inbred line MM27 plant, the inbred line MM27 will be stable while when crossed with another, different corn line, an $F_1$ hybrid seed is produced.

An inbred line has been produced through several cycles of self-pollination and is therefore to be considered as a homozygous line. An inbred line can also be produced though the dihaploid system which involves doubling the chromosomes from a haploid plant thus resulting in an inbred line that is genetically stable (homozygous) and can be reproduced without altering the inbred line. A hybrid variety is classically created through the fertilization of an ovule from an inbred parental line by the pollen of another, different inbred parental line. Due to the homozygous state of the inbred line, the produced gametes carry a copy of each parental chromosome.

As both the ovule and the pollen bring a copy of the arrangement and organization of the genes present in the parental lines, the genome of each parental line is present in the resulting $F_1$ hybrid, theoretically in the arrangement and organization created by the plant breeder in the original parental line.

As long as the homozygosity of the parental lines is maintained, the resulting hybrid cross is stable. The $F_1$ hybrid is then a combination of phenotypic characteristics issued from two arrangement and organization of genes, both created by a man skilled in the art through the breeding process.

Still further, this invention also is directed to methods for producing an inbred corn line MM27-derived corn plant by crossing inbred corn line MM27 with a second corn plant and growing the progeny seed, and repeating the crossing and growing steps with the inbred corn line MM27-derived plant from 0 to 7 times. Thus, any such methods using the inbred corn line MM27 are part of this invention: selfing, back-crosses, hybrid production, crosses to populations, and the like. All plants produced using inbred corn line MM27 as a parent are within the scope of this invention, including plants derived from inbred corn line MM27. Advantageously, the inbred corn line is used in crosses with other, different, corn inbreds to produce first generation ($F_1$) corn hybrid seeds and plants with superior characteristics.

It should be understood that the inbred can, through routine manipulation of cytoplasmic or other factors, be produced in a male-sterile form. Such embodiments are also contemplated within the scope of the present claims. As used herein, the term plant includes plant cells, plant protoplasts, plant cell tissue cultures from which corn plants can be regenerated, plant calli, plant clumps and plant cells that are intact in plants or parts of plants, such as embryos, pollen, ovules, flowers, kernels, seeds, ears, cobs, leaves, husks, stalks, roots, root tips, anthers, silk and the like.

Duncan, et al. (*Planta,* 1985, 165:322-332) indicates that 97% of the plants cultured that produced callus were capable of plant regeneration. Subsequent experiments with both inbreds and hybrids produced 91% regenerable callus that produced plants. In a further study in 1988, Songstad, et al. (*Plant Cell Reports,* 7:262-265) reports several media additions that enhance regenerability of callus of two inbred lines. Other published reports also indicated that "nontraditional" tissues are capable of producing somatic embryogenesis and plant regeneration. K. V. Rao et al., (*Maize Genetics Cooperation Newsletter,* 1986, 60:64-65) refer to somatic embryogenesis from glume callus cultures and B. V. Conger, et al. (*Plant Cell Reports,* 1987, 6:345-347) indicate somatic embryogenesis from the tissue cultures of corn leaf segments. Thus, it is clear from the literature that the state of the art is such that these methods of obtaining plants are routinely used and have a very high rate of success.

Tissue culture of corn is also described in European Patent Application, publication 160,390 and in Green and Rhodes, *Maize for Biological Research,* Plant Molecular Biology Association, Charlottesville, Va., 1982, 367-372. Thus, another aspect of this invention is to provide cells which upon growth and differentiation produce corn plants having the physiological and morphological characteristics of inbred corn line MM27.

The utility of inbred corn line MM27 also extends to crosses with other species. Commonly, suitable species will be of the family Graminaceae, and especially of the genera *Zea, Tripsacum, Coix, Schlerachne, Polytoca, Chionachne,* and *Trilobachne,* of the tribe Maydeae. Potentially suitable for crosses with MM27 may be the various varieties of grain sorghum, *Sorghum bicolor* (L.) Moench.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed inbred line. An embodiment of the present invention comprises at least one transformation event in MM27.

Plant transformation involves the construction of an expression vector which will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed corn plants, using transformation methods as described below to incorporate transgenes into the genetic material of the corn plant(s).

Expression Vectors for Corn Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which, when placed under the control of plant regulatory signals, confers resistance to kanamycin (Fraley et al., *Proc. Natl. Acad. Sci. U.S.A.,* 80:4803 (1983)). Another commonly used selectable marker gene is the hygromycin phosphotransferase gene which confers resistance to the antibiotic hygromycin (Vanden Elzen et al., *Plant Mol. Biol.,* 5:299 (1985)).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant (Hayford et al., *Plant Physiol.* 86:1216 (1988), Jones et al., *Mol. Gen. Genet.,* 210:86 (1987), Svab et al., *Plant Mol. Biol.* 14:197 (1990), and Hille et al., *Plant Mol. Biol.* 7:171 (1986)). Other selectable marker genes confer resistance to herbicides such as glyphosate, glufosinate or bromoxynil (Comai et al., *Nature* 317:741-744 (1985), Gordon-Kamm et al., *Plant Cell* 2:603-618 (1990) and Stalker et al., *Science* 242:419-423 (1988)).

Selectable marker genes for plant transformation that are not of bacterial origin include, for example, mouse dihydrofolate reductase, plant 5-enolpyruvylshikimate-3-phosphate synthase and plant acetolactate synthase (Eichholtz et al., Somatic Cell Mol. Genet. 13:67 (1987), Shah et al., *Science* 233:478 (1986), and Charest et al., *Plant Cell Rep.* 8:643 (1990)).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta-glucuronidase (GUS), beta-galactosidase, luciferase, and chloramphenicol acetyltransferase (Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), and DeBlock et al., *EMBO J.* 3:1681 (1984). Another approach to the identification of relatively rare transformation events has been use of a gene that encodes a dominant constitutive regulator of the *Zea mays* anthocyanin pigmentation pathway (Ludwig et al., *Science* 247:449 (1990)).

In vivo methods for visualizing GUS activity that do not require destruction of plant tissue are also available. However, these in vivo methods for visualizing GUS activity have not proven useful for recovery of transformed cells because of low sensitivity, high fluorescent backgrounds and limitations associated with the use of luciferase genes as selectable markers.

A gene encoding Green Fluorescent Protein (GFP) has been utilized as a marker for gene expression in prokaryotic and eukaryotic cells (Chalfie et al., *Science* 263:802 (1994)). GFP and mutants of GFP may be used as screenable markers.

Expression Vectors for Corn Transformation: Promoters

Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain organs, such as leaves, roots, seeds and tissues such as fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters—An inducible promoter is operably linked to a gene for expression in corn. Optionally, the inducible promoter is operably linked to a nucleotide sequence encoding a signal sequence which is operably linked to a gene for expression in corn. With an inducible promoter the rate of transcription increases in response to an inducing agent. Any inducible promoter can be used in the instant invention. See Ward et al., *Plant Mol. Biol.* 22:361-366 (1993). Exemplary inducible promoters include, but are not limited to, that from the ACEI system which responds to copper (Mett et al., *Proc. Natl. Acad. Sci. U.S.A.* 90:4567-4571 (1993)); In2 gene from maize which responds to benzenesulfonamide herbicide safeners (Gatz et al., *Mol. Gen. Genetics* 243:32-38 (1994)) or Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. U.S.A.* 88:0421 (1991)).

B. Constitutive Promoters—A constitutive promoter is operably linked to a gene for expression in corn or the constitutive promoter is operably linked to a nucleotide sequence encoding a signal sequence which is operably linked to a gene for expression in corn. Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)).

The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO96/30530.

C. Tissue-specific or Tissue-preferred Promoters—A tissue-specific promoter is operably linked to a gene for expression in corn. Optionally, the tissue-specific promoter is operably linked to a nucleotide sequence encoding a signal sequence which is operably linked to a gene for expression in corn. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11): 2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Knox, C., et al., *Plant Mol. Biol.* 9:3-17 (1987), Lerner et al., *Plant Physiol.* 91:124-129 (1989), Fontes et al., *Plant Cell* 3:483-496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., *Cell* 39:499-509 (1984), Stiefel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is corn. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology* CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant inbred line can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt alpha-endotoxin gene. Moreover, DNA molecules encoding alpha-endotoxin genes can be purchased from American Type Culture Collection, Manassas, Va., for example, under ATCC Accession Nos. 40098, 67136, 31995 and 31998.

C. A lectin. See, for example, the article by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US93/06487. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* alpha-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper-accumulation of a monoterpene, a sesquiterpene, a steroid, a hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance).

M. A membrane permease, a channel former or a channel blocker. For example, see the disclosure of Jaynes et al., *Plant Sci* 89:43 (1993), of heterologous expression of a cecropin-beta, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect.

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo-alpha-1,4-D-polygalacturonases facilitate fungal colonization and plant nutrient release by solubilizing plant cell wall homo-alpha-1,4-D-galacturonase. See Lamb et al., *BioTechnology* 10:1436 (1992). The cloning and characterization of a gene which encodes a bean endopolygalacturonase-inhibiting protein is described by Toubart et al., *Plant J.* 2:367 (1992).

R. A developmental-arrestive protein produced in nature by a plant. For example, Logemann et al., *BioTechnology* 10:305 (1992), have shown that transgenic plants expressing the barley ribosome-inactivating gene have an increased resistance to fungal disease.

2. Genes that Confer Resistance to an Herbicide, for Example:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvylshikimate-3-phosphate phosphate synthase (EPSP) and aroA genes, respectively) and other phosphono compounds such as glufosinate (phosphinothricin acetyl transferase (PAT) and *Streptomyces hygroscopicus* PAT bar genes), and pyridinoxy or phenoxy propionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *BioTechnology* 7:61 (1989), describe the production of transgenic plants that express chimeric bar genes coding for PAT activity. Exemplary of genes conferring resistance to phenoxy propionic acids and cyclohexones, such as sethoxydim and haloxyfop are rithe Acc1-S1, Acc1-S2 and Acc1-S3 genes described by Marshall et al., *Theor. Appl. Genet.* 83:435 (1992).

C. An herbicide that inhibits photosynthesis, such as a triazine (psbA and gs+ genes) or a benzonitrile (nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knutzon et al., *Proc. Natl. Acad. Sci. U.S.A.* 89:2624 (1992)

B. Increased resistance to high light stress such as photooxidative damages, for example by transforming a plant with a gene coding for a protein of the Early Light Induced Protein family (ELIP) as described in WO 03074713 in the name of Biogemma.

C. Modified carbohydrate composition effected, for example, by transforming plants with a gene coding for an enzyme that alters the branching pattern of starch. See Shiroza et al., *J. Bact.* 170:810 (1988) (nucleotide sequence of *Streptococcus mutants* fructosyltransferase gene), Steinmetz et al., *Mol. Gen. Genet.* 20:220 (1985) (nucleotide sequence of *Bacillus subtilis* levansucrase gene), Pen et al., *BioTechnology* 10:292 (1992) (production of transgenic plants that express *Bacillus lichenifonnis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley alpha-amylase gene), and Fisher et al., *Plant Physiol.* 102:1045 (1993) (maize endosperm starch branching enzyme II).

D. Increased resistance/tolerance to water stress or drought, for example, by transforming a plant to create a plant having a modified content in ABA-Water-Stress-Ripening-Induced proteins (ARS proteins) as described in WO 0183753 in the name of Biogemma, or by transforming a plant with a nucleotide sequence coding for a phosphoenolpyruvate carboxylase as shown in WO02081714. The tolerance of corn to drought can also be increased by an overexpression of phosphoenolpyruvate carboxylase (PEPC-C4), obtained, for example from *sorghum*.

E. Increased content of cysteine and glutathione, useful in the regulation of sulfur compounds and plant resistance against various stresses such as drought, heat or cold, by transforming a plant with a gene coding for an Adenosine 5' Phosphosulfate as shown in WO 0149855.

F. Increased nutritional quality, for example, by introducing a zein gene which genetic sequence has been modified so that its protein sequence has an increase in lysine and proline. The increased nutritional quality can also be attained by introducing into the maize plant an albumin 2S gene from sunflower that has been modified by the addition of the KDEL peptide sequence to keep and accumulate the albumin protein in the endoplasmic reticulum.

G. Decreased phytate content: 1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. In maize, this, for example, could be accomplished, by cloning and then reintroducing DNA associated with the single allele which is responsible for maize mutants characterized by low levels of phytic acid. See Raboy et al., *Maydica* 35:383 (1990).

4. Genes that Control Male Sterility

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., *Plant Mol. Biol.* 19:611-622,1992).

Examples of Transgenes

MON810 (also designated as MON810BT1 or BT1) is the designation given by the Monsanto Company (St. Louis, Mo.) for the transgenic event that, when expressed in maize, produces an endotoxin that is efficacious against the European corn borer, *Ostrinia nubilalis* and certain other Lepidopteran larvae.

MON603 (also designated as MON603RR2 or RR2), better known as NK603, is the designation for the transgenic event that, when expressed in maize, allows the use of glyphosate as a weed control agent on the crop. Another transgenic event, GA21, when expressed in maize, also allows the use of glyphosate as a weed control agent on the crop.

MON863 (also designated as MON863CRW2 or CRW2) is the designation for the transgenic event that, when expressed in maize, produces an endotoxin that is efficacious against the corn root worm, *Diabrotica vigifera*, and certain other Coleopteran larvae.

MON88017 (also designated as MON88017CCR2 or CCR2) is the transgenic event that, when expressed in maize, allows the use of glyphosate as a weed control agent. In addition, this event produces an endotoxin that is efficacious against the corn root worm, *Diabrotica virgifera*, and certain other Coleopteran larvae.

HERCULEX Corn Borer, better known as HX1 or TC1507, is the designation for the transgenic event that, when expressed in maize, produces an endotoxin that is efficacious against the European corn borer, *Ostrinia nubilalis*, and certain other Lepidopteran larvae. In addition, the transgenic event was developed to allow the crop to be tolerant to the use of glufosinate ammonium, the active ingredient in phosphinothricin herbicides.

HERCULEX Root Worm HXT, or DAS59122-7, is the designation for the transgenic event that, when expressed in maize, produces an endotoxin that is efficacious against the corn root worm, *Diabrotica virgifera*, and certain other Coleopteran larvae. In addition, the transgenic event was developed to allow the crop to be tolerant to the use of glufosinate ammonium, the active ingredient in phosphinothricin herbicides.

T25 (also designated as T25LL) is the designation for the transgenic event that, when expressed in maize, allows the crop to be tolerant to the use of glufosinate ammonium, the active ingredient in phosphinothricin herbicides.

Methods for Corn Transformation

Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,591,616 issued Jan. 7, 1997.

B. Direct Gene Transfer—Despite the fact the host range for *Agrobacterium*-mediated transformation is broad, some major cereal crop species and gymnosperms have generally been recalcitrant to this mode of gene transfer, even though some success has recently been achieved in rice and corn. Hiei et al., *The Plant Journal* 6:271-282 (1994) and U.S. Pat. No. 5,591,616 issued Jan. 7, 1997. Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 micron: The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *BioTechnology* 6:559-563 (1988), Sanford, J. C., *Physiol Plant* 7:206 (1990), Klein et al., *BioTechnology* 10:268 (1992). In corn, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang et al., *BioTechnology* 9:996 (1991). Alternatively, liposome and spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues have also been described. D'Halluin et al., *Plant Cell* 4:1495-1505 (1992) and Spencer et al., *Plant Mol. Biol.* 24:51-61 (1994).

Following transformation of corn target tissues, expression of the above-described selectable marker genes allows for preferential selection of transformed cells, tissues and/or plants, using regeneration and selection methods now well known in the art.

The foregoing methods for transformation would typically be used for producing a transgenic inbred line. The transgenic inbred line could then be crossed, with another (non-transformed or transformed) inbred line, in order to produce a new transgenic inbred line. Alternatively, a genetic trait which has been engineered into a particular corn line using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term inbred corn plant is used in the context of the present invention, this also includes any inbred corn plant where one or more desired trait has been introduced through backcrossing methods, whether such trait is a naturally occurring one or a transgenic one. Backcrossing methods can be used with the present invention to improve or introduce one or more characteristic into the inbred. The term backcrossing as used herein refers to the repeated crossing of a hybrid progeny back to one of the parental corn plants for that inbred. The parental corn plant which contributes the gene or the genes for the desired characteristic is termed the nonrecurrent or donor parent. This terminology refers to the fact that the nonrecurrent parent is used one time in the backcross protocol and therefore does not recur. The parental corn plant to which the gene or genes from the nonrecurrent parent are transferred is known as the recurrent parent as it is used for several rounds in the backcrossing protocol (Fehr, 1987).

In a typical backcross protocol, the original inbred of interest (recurrent parent) is crossed to a second inbred (nonrecurrent parent) that carries the gene or genes of interest to be transferred. The resulting progeny from this cross are then crossed again to the recurrent parent and the process is repeated until a corn plant is obtained wherein all the desired morphological and physiological characteristics of the recurrent parent are recovered in the converted plant in addition to the gene or genes transferred from the nonrecurrent parent. It should be noted that some, one, two, three or more, self-pollination and growing of a population might be included between two successive backcrosses. Indeed, an appropriate selection in the population produced by the self-pollination, i.e. selection for the desired trait and physiological and morphological characteristics of the recurrent parent might be equivalent to one, two or even three additional backcrosses in a continuous series without rigorous selection, saving time, money and effort for the breeder. A non limiting example of such a protocol would be the following: a) the first generation $F_1$ produced by the cross of the recurrent parent A by the donor parent B is backcrossed to parent A, b) selection is practiced for the plants having the desired trait of parent B, c) selected plants are self-pollinated to produce a population of plants where selection is practiced for the plants having the desired trait of parent B and the physiological and morphological characteristics of parent A, d) the selected plants are backcrossed one, two, three, four, five or more times to parent A to produce selected backcross progeny plants comprising the desired trait of parent B and the physiological and morphological characteristics of parent A. Step c) may or may not be repeated and included between the backcrosses of step d.

The selection of a suitable recurrent parent is an important step for a successful backcrossing procedure. The goal of a backcross protocol is to alter or substitute one or more trait(s) or characteristic(s) in the original inbred. To accomplish this, a gene or genes of the recurrent inbred is modified or substituted with the desired gene or genes from the nonrecurrent parent, while retaining essentially all of the rest of the desired genetic, and therefore the desired physiological and morphological, constitution of the original inbred. The choice of the particular nonrecurrent parent will depend on the purpose of the backcross; one of the major purposes is to add some commercially desirable, agronomically important trait(s) to the plant. The exact backcrossing protocol will depend on the characteristic(s) or trait(s) being altered to determine an appropriate testing protocol. Although backcrossing methods are simplified when the characteristic being transferred is a single gene and dominant allele, multiple genes and recessive allele(s) may also be transferred and therefore, backcross breeding is by no means restricted to character(s) governed by one or a few genes. In fact the number of genes might be less important than the identification of the character(s) in the segregating population. In this instance it may then be necessary to introduce a test of the progeny to determine if the desired characteristic(s) has been successfully transferred. Such tests encompass not only visual inspection and simple crossing, but also follow up of the characteristic(s) through genetically associated markers and molecular assisted breeding tools. For example, selection of progeny containing the transferred trait is done by direct selection, visual inspection for a trait associated with a dominant allele, while the selection of progeny for a trait that is transferred via a recessive allele, such as the waxy starch characteristic, require selfing the progeny to determine which plant carry the recessive allele(s).

Many single gene traits have been identified that are not regularly selected for in the development of a new inbred but that can be improved by backcrossing techniques. Single gene traits may or may not be transgenic, i.e. they may be naturally present in the non recurrent parent, examples of these traits include but are not limited to, male sterility, waxy starch, amylose starch, herbicide resistance, resistance for bacterial, fungal, or viral disease, insect resistance, male fertility, water stress tolerance, enhanced nutritional quality, industrial usage, increased digestibility yield stability and yield enhancement. An example of this is the Rp1D gene which controls resistance to rust fungus by preventing *P. sorghi* from producing spores. The Rp1D gene is usually preferred over the other Rp genes because it is widely effective against all races of rust, but the emergence of new races has lead to the use of other Rp genes comprising, for example, the Rp1E, Rp1G, Rp1I, Rp1K or "compound" genes which combine two or more Rp genes including Rp1GI, Rp1GDJ, etc. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

In 1981, the backcross method of breeding accounted for 17% of the total breeding effort for inbred line development in the United States, according to, Hallauer, A. R. et al. (1988) "Corn Breeding" in *Corn and Corn Improvement*, No. 18, pp. 463-481. The backcross breeding method provides a precise way of improving varieties that excel in a large number of attributes but are deficient in a few characteristics (Allard, 1960, *Principles of Plant Breeding*, John Wiley & Sons, Inc.).

The method makes use of a series of backcrosses to the variety to be improved during which the character or the characters in which improvement is sought is maintained by selection. At the end of the backcrossing, the gene or genes being transferred unlike all other genes will be heterozygous. Selfing after the last backcross produces homozygosity for this gene pair(s) and, coupled with selection, will result in a variety with exactly the adaptation, yielding ability and quality characteristics of the recurrent parent but superior to that parent in the particular characteristic(s) for which the improvement program was undertaken. Therefore, this method provides the plant breeder with a high degree of genetic control of his work.

The method is scientifically exact because the morphological and agricultural features of the improved variety could be described in advance and because the same variety could, if it were desired, be bred a second time by retracing the same steps (Briggs, "Breeding wheats resistant to bunt by the backcross method", 1930 *Jour. Amer. Soc. Agron.*, 22: 289-244).

Backcrossing is a powerful mechanism for achieving homozygosity and any population obtained by backcrossing must rapidly converge on the genotype of the recurrent parent. When backcrossing is made the basis of a plant breeding program, the genotype of the recurrent parent will be modified only with regards to genes being transferred, which are maintained in the population by selection.

Examples of successful backcrosses are the transfer of stem rust resistance from "Hope" wheat to "Bart" wheat and the transfer of bunt resistance to "Bart" wheat to create "Bart 38" which has resistance to both stem rust and bunt. Also highlighted by Allard is the successful transfer of mildew, leaf spot and wilt resistances in "California Common" alfalfa to create "Caliverde". This new "Caliverde" variety produced through the backcross process is indistinguishable from "California Common" except for its resistance to the three named diseases.

One of the advantages of the backcross method is that the breeding program can be carried out in almost every environment that will allow the development of the character being transferred. Another advantage of the backcross method is that more than one character or trait can be transferred, either through several backcrosses or through the use of transformation and then backcrossing.

The backcross technique is not only desirable when breeding for disease resistance but also for the adjustment of morphological characters, color characteristics and simply inherited quantitative characters such as earliness, plant height and seed size and shape. In this regard, a medium grain type variety, "Calady", has been produced by Jones and Davis. In dealing with quantitative characteristics, they selected the donor parent with the view of sacrificing some of the intensity of the character for which it was chosen, i.e. grain size. "Lady Wright", a long grain variety was used as the donor parent and "Coloro", a short grain one as the recurrent parent. After four backcrosses, the medium grain type variety "Calady" was produced.

Industrial Applicability

Corn is used as human food, livestock feed, and as raw material in industry. The food uses of corn, in addition to human consumption of corn kernels, include both products of dry- and wet-milling industries. The principal products of corn dry-milling are grits, meal and flour. The corn wet-milling industry can provide corn starch, corn syrups, and dextrose for food use. Corn oil is recovered from corn germ, which is a by-product of both dry- and wet-milling industries.

Corn, including both grain and non-grain portions of the plant, is also used extensively as livestock feed, primarily for beef cattle, dairy cattle, hogs and poultry. Industrial uses of corn include production of ethanol, corn starch in the wet-milling industry and corn flour in the dry-milling industry. The industrial applications of corn starch and flour are based on functional properties, such as viscosity, film formation, adhesive properties, and ability to suspend particles. Corn starch and flour have application in the paper and textile industries. Other industrial uses include applications in adhesives, building materials, foundry binders, laundry starches, explosives, oil-well muds and other mining applications.

Plant parts other than the grain of corn are also used in industry, for example, stalks and husks are made into paper and wallboard and cobs are used for fuel and to make charcoal.

The seed of inbred corn line MM27, the plant produced from the inbred seed, the hybrid corn plant produced from the crossing of the inbred, hybrid seed, and various parts of the hybrid corn plant and transgenic versions of the foregoing, can be utilized for human food, livestock feed, and as a raw material in industry.

Tables of Field Test Trials

In the tables that follow, the traits and characteristics of hybrid combinations having inbred corn line MM27 as a parental line are given compared to other hybrids. The data collected are presented for key characteristics and traits. The field tests are experimental trials and have been made at numerous locations, with one or two replications per location. Information about these experimental hybrids as compared to the check hybrids is presented.

There may be a pedigree listed in the comparison group of the hybrid(s) containing an inbred parent with the nomenclatures MON88017, Bt1, RR2, CRW2, etc. following the inbred name. Such designations of the trangenes are mentioned hereabove. Information for each pedigree includes:

1. The number of direct comparisons between the two hybrids (# Comp) is shown in column 2.

2. The percentage of times each hybrid wins for grain yield in the direct comparison (% Wins) is shown in column 3.

3. The mean for the percentage of moisture (% H2O) of the grain for the hybrid across all is shown in column 4.

4. The grain yield (bushels/acre) of the hybrid across all locations is shown in column 5.

5. The test weight which is the grain density as measured in pounds per bushel is shown in column 6.

6. The number of plants per acre averaged across all locations (Plant Popn) is shown in column 7.

7. A mean of the percentage of plants with stalk lodging (% SL) across all locations is shown in column 8.

8. A mean of the percentage of plants with root lodging (% RL) across all locations is shown in column 9.

9. The average gross income per acre for a hybrid based on $3.00 per bushel corn and $0.035 needed to dry one bushel of corn one percentage point of moisture to a base moisture of 15.5% is shown in column 10.

TABLE 2

Head to Head Comparisons:

| Pedigree | # Comp | % Wins | % H2O | Grain Yield | TW | Plant Popn | % SL | % RL | $ Acre |
|---|---|---|---|---|---|---|---|---|---|
| BB14 × MM27 | 56 | 68 | 17.6 | 191.8 | 56.6 | 31375 | 3.0 | 1.5 | 558.04 |
| BB14 × LH185BT1 | 56 | 32 | 17.9 | 180.8 | 56.9 | 31523 | 2.7 | 1.4 | 524.40 |
| BB14 × MM27 | 79 | 47 | 19.2 | 195.1 | 55.9 | 30430 | 1.8 | 0.8 | 557.25 |
| BB14 × LH287BT1 | 79 | 53 | 20.0 | 196.6 | 55.8 | 30714 | 2.3 | 2.1 | 555.30 |
| CB1 × MM27 | 44 | 52 | 17.5 | 198.6 | 55.2 | 29264 | 1.4 | 0.6 | 577.83 |
| CB1 × LH287 | 44 | 48 | 17.7 | 196.7 | 55.6 | 29308 | 1.1 | 0.7 | 570.7 |
| CB1 × MM27 | 89 | 42 | 19.4 | 200.5 | 54.9 | 29653 | 1.7 | 0.5 | 570.56 |
| CB1 × LH287BT1 | 89 | 58 | 20.4 | 202.1 | 54.9 | 30473 | 2.8 | 2.4 | 567.40 |
| CB1 × MM27 | 42 | 55 | 16.8 | 203.4 | 57.3 | 30708 | 1.7 | 0.5 | 596.31 |
| CB1 × LH324BT1 | 42 | 45 | 16.6 | 200.0 | 57.7 | 30983 | 1.2 | 0.3 | 588.20 |

TABLE 3

Head to Head Comparisons

| Pedigree | # Comp | % Wins | % H2O | Grain Yield | TW | Plant Popn | % SL | % RL | $ Acre |
|---|---|---|---|---|---|---|---|---|---|
| BB38 × MM27 | 29 | 62 | 16.1 | 199.9 | 57.2 | 30708 | 2.5 | 0.3 | 590.02 |
| DEKALB 63-79 | 29 | 38 | 16.4 | 191.3 | 57.8 | 30983 | 2.1 | 4.4 | 563.73 |
| BB45 × MM27 | 10 | 70 | 19.3 | 204.3 | 55.9 | 31298 | 1.7 | 0.0 | 580.74 |
| CB1 × UNW1BT1 | 10 | 30 | 17.9 | 194.9 | 56.7 | 30020 | 1.8 | 0.7 | 564.01 |
| BB47 × MM27 | 17 | 47 | 18.1 | 199.0 | 56.3 | 30628 | 2.3 | 0.0 | 575.45 |
| HC53RR2 × LH324BT1CRW2 | 17 | 53 | 19.9 | 199.7 | 55.4 | 30501 | 0.4 | 6.5 | 564.23 |
| BB53 × MM27 | 17 | 65 | 17.9 | 200.5 | 56.2 | 29141 | 2.4 | 1.6 | 580.18 |
| CB1 × LH324BT1 | 17 | 35 | 17.6 | 195.4 | 57.5 | 30461 | 3.1 | 3.9 | 567.44 |
| BB57 × MM27 | 7 | 71 | 15.1 | 201.1 | 58.3 | 31052 | 1.4 | 0.0 | 602.60 |
| LH331RR2 × UNW1BT1 | 7 | 29 | 14.3 | 185.5 | 58.9 | 29733 | 0.9 | 0.0 | 560.61 |
| BB57 × MM27 | 15 | 67 | 18.4 | 206.0 | 56.0 | 31401 | 3.1 | 0.0 | 594.05 |
| HXN111CRW2RR2 × UNW1BT1 | 15 | 33 | 18.3 | 199.9 | 57.0 | 31023 | 0.3 | 0.4 | 576.36 |
| BB59 × MM27 | 19 | 58 | 15.6 | 194.3 | 57.7 | 30363 | 0.1 | 0.0 | 576.94 |
| CB1 × UNW1 | 19 | 42 | 16.0 | 188.9 | 57.9 | 31384 | 0.7 | 0.5 | 557.07 |
| BC5 × MM27 | 42 | 57 | 19.7 | 191.8 | 55.6 | 29755 | 1.6 | 0.1 | 543.51 |
| CB1 × UNW1 | 42 | 43 | 21.3 | 192.5 | 55.4 | 29674 | 1.3 | 1.3 | 534.99 |
| HXN110RR2 × MM27 | 45 | 64 | 16.6 | 205.7 | 57.4 | 30339 | 1.4 | 0.4 | 604.94 |
| CB1 × UNW1BT1 | 45 | 36 | 16.8 | 198.3 | 57.2 | 30260 | 1.0 | 0.6 | 581.58 |
| HXN110RR2 × MM27 | 46 | 83 | 16.4 | 203.6 | 57.5 | 30276 | 1.3 | 0.3 | 599.63 |
| FR3913 × UNW1BT1 | 46 | 17 | 17.3 | 189.4 | 57.3 | 29675 | 1.0 | 0.2 | 551.36 |
| HXN110RR2 × MM27 | 11 | 73 | 22.0 | 196.9 | 55.7 | 30265 | 1.3 | 4.8 | 542.03 |
| HXN110RR2 × UNW1 | 11 | 37 | 21.5 | 183.6 | 56.4 | 29889 | 2.1 | 12.7 | 507.83 |
| HXN112CRW2RR2 × MM27 | 15 | 53 | 20.3 | 207.5 | 55.2 | 30799 | 2.1 | 1.3 | 585.47 |
| HXN111CRW2RR2 × UNW1BT1 | 15 | 47 | 18.3 | 199.9 | 57.0 | 31023 | 0.3 | 0.4 | 576.36 |
| HXN11RR2 × MM27 | 16 | 50 | 18.5 | 201.1 | 56.0 | 30708 | 1.7 | 0.5 | 596.31 |
| HXN111CRW2RR2 × UNW1BT1 | 16 | 50 | 18.4 | 199.3 | 56.9 | 30983 | 1.2 | 0.3 | 588.20 |
| RBO1BT1 × MM27 | 11 | 64 | 15.7 | 158.0 | 58.9 | 24687 | 5.5 | 11.0 | 465.93 |
| BB23 × HXN4BT1CRW2 | 11 | 36 | 15.2 | 149.0 | 58.9 | 24101 | 0.9 | 9.9 | 442.83 |
| RBO1BT1 × MM27 | 63 | 78 | 16.0 | 191.3 | 57.1 | 28955 | 2.0 | 1.2 | 567.16 |
| BB45 × UNW1BT1 | 63 | 22 | 17.1 | 179.5 | 57.5 | 28720 | 7.1 | 7.8 | 525.34 |
| RBO1BT1 × MM27 | 44 | 55 | 18.2 | 190.9 | 56.6 | 29857 | 0.5 | 0.2 | 551.00 |
| CB1 × UNW1 | 44 | 45 | 20.9 | 190.9 | 55.5 | 30074 | 0.7 | 1.5 | 533.34 |
| RBO1BT1 × MM27 | 44 | 84 | 18.2 | 190.9 | 56.6 | 29857 | 0.5 | 0.2 | 551.00 |
| WBB53 × UNW1 | 44 | 16 | 19.2 | 173.2 | 56.7 | 29903 | 1.9 | 0.3 | 493.62 |
| TR7245HX1-1 × MM27 | 9 | 67 | 18.7 | 195.4 | 55.8 | 31210 | 2.0 | 8.2 | 561.27 |
| BB38 × SGI973HX1 | 9 | 33 | 22.9 | 187.8 | 54.5 | 29687 | 0.1 | 0.0 | 511.45 |
| BB53 × MM27 | 17 | 65 | 17.9 | 200.5 | 56.2 | 29141 | 2.4 | 1.6 | 580.18 |
| SGI890HX1-1 × LH287 | 17 | 35 | 19.3 | 195.0 | 56.3 | 31283 | 3.4 | 10.7 | 555.15 |
| BC109 × MM27 | 15 | 47 | 17.6 | 200.7 | 56.7 | 31544 | 2.7 | 0.1 | 583.19 |
| FR3912 × UNW1BT1 | 15 | 57 | 17.5 | 197.9 | 56.9 | 30788 | 2.4 | 0.0 | 575.87 |
| BC109 × MM27 | 15 | 67 | 17.6 | 200.7 | 56.7 | 31544 | 2.7 | 0.1 | 583.19 |
| GP282 × UNW1BT1 | 15 | 33 | 17.3 | 196.5 | 57.2 | 31344 | 2.1 | 0.3 | 573.65 |
| BB14 × MM27BT1 | 9 | 57 | 20.4 | 198.9 | 55.6 | 30978 | 0.2 | 0.0 | 564.90 |
| BB14 × MM27 | 9 | 43 | 18.7 | 197.6 | 56.0 | 31284 | 0.7 | 0.4 | 555.30 |

Deposit Information

A deposit of the Limagrain Europe S.A. and KWS SART AG proprietary Inbred Corn Line MM27 disclosed above and recited in the appended claims has been made with the American Type Culture Collection (ATCC), 10801 University Boulevard, Manassas, Va. 20110. The date of deposit was May 27, 2010. The deposit of 2,500 seeds was taken from the same deposit maintained by AgReliant Genetics, LLC since prior to the filing date of this application. All restrictions will be removed upon granting of a patent, and the deposit is intended to meet all of the requirements of 37 C.F.R. §§1.801-1.809. The ATCC Accession Number is PTA-11001. The deposit will be maintained in the depository for a period of thirty years, or five years after the last request, or for the enforceable life of the patent, whichever is longer, and will be replaced as necessary during that period.

What is claimed is:

1. A seed of corn inbred line designated MM27, wherein a representative sample of seed of said line was deposited under ATCC Accession No. PTA-11001.

2. A corn plant, or a part thereof, produced by growing the seed of claim 1.

3. A corn plant, or a part thereof, having all the physiological and morphological characteristics of the inbred line MM27, wherein a representative sample of seed of said line was deposited under ATCC Accession No. PTA-11001.

4. A tissue culture of cells produced from the plant of claim 2, wherein said cells of the tissue culture are produced from a plant part selected from the group consisting of leaves, pollen, embryos, roots, root tips, anthers, silks, flowers, kernels, ears, cobs, husks, seeds and stalks.

5. A corn plant regenerated from the tissue culture of claim 4, wherein the regenerated plant has all the morphological and physiological characteristics of inbred line MM27, wherein a representative sample of seed of said line was deposited under ATCC Accession No. PTA-11001.

6. A method for producing a hybrid corn seed wherein the method comprises crossing the plant of claim 2 with a different corn plant and harvesting the resultant hybrid corn seed.

7. A hybrid corn seed produced by the method of claim 6.

8. A method for producing inbred line MM27, wherein a representative sample of seed of said line was deposited under ATCC Accession No. PTA-11001, wherein the method comprises:
 a) planting a collection of seed comprising seed of a hybrid, one of whose parents is inbred line MM27, said collection also comprising seed of said inbred;
 b) growing plants from said collection of seed;
 c) identifying the plants having the physiological and morphological characteristics of corn inbred line MM27 as inbred parent plants;
 d) controlling pollination of said inbred parent plants in a manner which preserves the homozygosity of said inbred parent plant; and
 e) harvesting the resultant seed.

9. The method of claim 8 wherein step (c) comprises identifying plants with decreased vigor compared to the other plants grown from the collection of seeds.

10. A method for producing a corn plant that contains in its genetic material one or more transgenes, wherein the method comprises crossing the corn plant of claim 2 with either a second plant of another corn line which contains a transgene or a transformed corn plant of the inbred corn line MM27, so that the genetic material of the progeny that results from the cross contains the transgene(s) operably linked to a regulatory element and wherein the transgene confers a trait selected from the group consisting of male sterility, male fertility, herbicide resistance, insect resistance, disease resistance, water stress tolerance, and increased digestibility.

11. A corn plant, or a part thereof, produced by the method of claim 10.

12. The corn plant of claim 11, wherein the transgene confers resistance to an herbicide selected from the group consisting of imidazolinone, sulfonylurea, glyphosate, glufosinate, L-phosphinothricin, triazine and benzonitrile.

13. The corn plant of claim 11, wherein the transgene encodes a *Bacillus thuringiensis* protein.

14. The corn plant of claim 11, wherein the transgene confers disease resistance.

15. The corn plant of claim 11, wherein the transgene confers water stress tolerance.

16. The corn plant of claim 11, where in the transgene confers increased digestibility.

17. A method for producing a hybrid corn seed wherein the method comprises crossing the plant of claim 11 with a different corn plant and harvesting the resultant hybrid corn seed.

18. A method of producing a corn plant with waxy starch or increased amylose starch wherein the method comprises transforming the corn plant of claim 2 with a transgene that modifies carbohydrate metabolism.

19. A corn plant produced by the method of claim 18.

20. A method of introducing a desired trait into corn inbred line MM27 wherein the method comprises:
 a) crossing the inbred line MM27 plants grown from the inbred line MM27 seed, wherein a representative sample of seed of said line was deposited under ATCC Accession No. PTA-11001, with plants of another corn line that comprise a desired trait to produce progeny plants, wherein the desired trait is selected from the group consisting of male sterility, male fertility, herbicide resistance, insect resistance, disease resistance, waxy starch, water stress tolerance, increased amylose starch and increased digestibility;
 b) selecting progeny plants that have the desired trait to produce selected progeny plants;
 c) crossing the selected progeny plants with the inbred line MM27 plants to produce backcross progeny plants;
 d) selecting for backcross progeny plants that have the desired trait and physiological and morphological characteristics of corn inbred line MM27 listed in Table 1 to produce selected backcross progeny plants; and
 e) repeating steps (c) and (d) one or more times in succession to produce selected second or higher backcross progeny plants that comprise the desired trait and all the physiological and morphological characteristics of corn inbred line MM27 as listed in Table 1.

21. A corn plant produced by the method of claim 20, wherein the plant has the desired trait and all of the physiological and morphological characteristics of corn inbred line MM27 as listed in Table 1.

22. A method for producing inbred line MM27 seed, wherein a representative sample of seed of said line was deposited under ATCC Accession No. PTA-11001, wherein the method comprises crossing a first inbred parent corn plant with a second inbred parent corn plant and harvesting the resultant corn seed, wherein both said first and second inbred corn plant are the corn plant of claim 3.

23. A method for producing inbred line MM27 seed, wherein a representative sample of seed of said line was deposited under ATCC Accession No. PTA-11001, wherein the method comprises:
 a) planting an inbred corn seed of claim 1;
 b) growing a plant from said seed;
 c) controlling pollination in a manner that the pollen produced by the grown plant pollinates the ovules produced by the grown plant; and harvesting the resultant seed.

24. An $F_1$ hybrid corn plant having inbred line MM27 or a transgenic inbred line of MM27 as a parental line of said hybrid, wherein a representative sample of seed of MM27 was deposited under ATCC Accession No. PTA-11001 and wherein the transgenic inbred line MM27 or a second parental line comprises a transgene that confers a trait selected from the group consisting of disease resistance, male sterility, herbicide resistance, and insect resistance.

25. A method of introducing a desired trait into corn inbred line MM27 wherein the method comprises:
  a) crossing an inbred line MM27 plant grown from the inbred line MM27 seed, wherein a representative sample of seed of said line was deposited under ATCC Accession No. PTA-11001, with a donor corn plant comprising a mutant gene or transgene conferring a desired trait;
  b) selecting an $F_1$ progeny plant comprising the mutant gene or transgene conferring the desired trait;
  c) crossing the selected $F_1$ progeny plants with the inbred line MM27 plants to produce backcross progeny plants;
  d) selecting for backcross progeny plants that have the desired trait and physiological and morphological characteristics of corn inbred line MM27 listed in Table 1 to produce selected backcross progeny plants; and
  e) repeating steps (c) and (d) three or more times in succession to produce selected fourth or higher backcross progeny plants that comprise the mutant gene or transgene conferring the desired trait and all the physiological and morphological characteristics of corn inbred line MM27 as listed in Table 1.

26. A method of introducing a desired trait into corn inbred line MM27 wherein the method comprises:
  a, obtaining a molecular marker profile of corn inbred line MM27;
  b, crossing an inbred line MM27 plant grown from the inbred line MM27 seed, wherein a representative sample of seed of said line was deposited under ATCC Accession No. PTA-11001, with a donor corn plant comprising a mutant gene or transgene conferring a desired trait;
  c, using the molecular marker profile of corn inbred line MM27 to select an $F_1$ progeny plant with the desired trait and the molecular marker profile of corn inbred line MM27;
  d, crossing the selected $F_1$ progeny plants with the inbred line MM27 plants to produce backcross progeny plants; and
  e, repeating steps (c) and (d) three or more times in succession to produce selected fourth or higher backcross progeny plants that comprise the mutant gene or transgene conferring the desired trait and all the physiological and morphological characteristics of corn inbred line MM27 as listed in Table 1.

27. A method of producing an $F_1$ hybrid corn seed comprising crossing the backcross progeny plant of claim 25 with a different corn plant to produce an $F_1$ hybrid corn seed comprising a mutant gene or transgene comprising a desired trait.

28. A method of producing an $F_1$ hybrid corn seed comprising crossing the backcross progeny plant of claim 26 with a different corn plant to produce an $F_1$ hybrid corn seed comprising a mutant gene or transgene comprising a desired trait.

* * * * *